(12) United States Patent
Zhang et al.

(10) Patent No.: US 9,107,630 B2
(45) Date of Patent: *Aug. 18, 2015

(54) ULTRASOUND IMAGING SYSTEM WITH PIVOTING BREAST COMPRESSION PLATES

(75) Inventors: Heidi D. Zhang, Los Gatos, CA (US);
Robert F. Lawrence, Soquel, CA (US);
Gilbert M. Lima, Fremont, CA (US);
Steven C. Miller, Waukesha, WI (US);
Anne L. Hall, New Berlin, WI (US)

(73) Assignee: GENERAL ELECTRIC COMPANY, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/762,181

(22) Filed: Apr. 16, 2010
(Under 37 CFR 1.47)

(65) Prior Publication Data

US 2010/0204580 A1 Aug. 12, 2010

Related U.S. Application Data

(63) Continuation of application No. 10/616,319, filed on Jul. 9, 2003, now Pat. No. 7,806,827.

(60) Provisional application No. 60/453,644, filed on Mar. 11, 2003.

(51) Int. Cl.
*A61B 8/08* (2006.01)
*A61B 8/00* (2006.01)
*G01S 7/52* (2006.01)
*G01S 15/89* (2006.01)

(52) U.S. Cl.
CPC ............ *A61B 8/4218* (2013.01); *A61B 8/0825* (2013.01); *A61B 8/42* (2013.01); *G01S 7/52079* (2013.01); *G01S 15/899* (2013.01); *G01S 15/8915* (2013.01); *G01S 15/8938* (2013.01)

(58) Field of Classification Search
USPC .............................. 600/437, 459, 472; 378/37
See application file for complete search history.

(56) References Cited

U.S. PATENT DOCUMENTS

| | | | |
|---|---|---|---|
| 3,585,847 A | 6/1971 | Brenden | |
| 3,765,403 A | 10/1973 | Brenden | |
| 4,075,883 A | 2/1978 | Glover | |
| 4,409,838 A | 10/1983 | Schomberg | |
| 4,669,311 A | 6/1987 | McKinnon | |
| 5,033,456 A | 7/1991 | Pell et al. | |
| 5,044,053 A | 9/1991 | Kopel et al. | |
| 5,058,593 A | 10/1991 | Forestieri et al. | |

(Continued)

FOREIGN PATENT DOCUMENTS

| | | |
|---|---|---|
| EP | 0480086 | 4/1992 |
| EP | 0635238 | 7/1994 |

(Continued)

*Primary Examiner* — Parikha Mehta
(74) *Attorney, Agent, or Firm* — McAndrews, Held & Malloy, Ltd.; Jacob Groethe (57) ABSTRACT

An ultrasound breast imaging assembly includes first and second compression plates angled with respect to one another, a breast compression area defined between the first and second compression plates, at least one pivot assembly, and an ultrasound probe. The pivot assembly allows relative motion between the first and second compression plates. The ultrasound probe, which is configured to translate over one of the first and second compression plates, includes an active matrix array (AMA) positioned on one of the first and second compression plates.

31 Claims, 9 Drawing Sheets

(56) References Cited

U.S. PATENT DOCUMENTS

| | | | |
|---|---|---|---|
| 5,070,879 | A | 12/1991 | Herres |
| 5,103,129 | A | 4/1992 | Slayton et al. |
| 5,107,841 | A | 4/1992 | Sturgill |
| 5,117,832 | A | 6/1992 | Sanghvi et al. |
| 5,119,342 | A | 6/1992 | Harrison et al. |
| 5,121,361 | A | 6/1992 | Harrison et al. |
| 5,123,417 | A | 6/1992 | Walker et al. |
| 5,140,558 | A | 8/1992 | Harrison et al. |
| 5,170,792 | A | 12/1992 | Sturgill et al. |
| 5,174,298 | A | 12/1992 | Dolfi et al. |
| 5,175,709 | A | 12/1992 | Slayton et al. |
| 5,182,728 | A | 1/1993 | Shen et al. |
| 5,188,112 | A | 2/1993 | Sturgill et al. |
| 5,205,175 | A | 4/1993 | Garza et al. |
| 5,213,103 | A | 5/1993 | Martin et al. |
| 5,291,893 | A | 3/1994 | Slayton |
| 5,293,873 | A | 3/1994 | Fang |
| 5,301,674 | A | 4/1994 | Erikson et al. |
| 5,318,028 | A | 6/1994 | Mitchell et al. |
| 5,349,954 | A | 9/1994 | Tiemann et al. |
| 5,379,642 | A | 1/1995 | Reckwerdt et al. |
| 5,433,202 | A | 7/1995 | Mitchell et al. |
| 5,474,072 | A | 12/1995 | Shmulewitz |
| 5,479,927 | A | 1/1996 | Shmulewitz |
| 5,506,877 | A | 4/1996 | Niklason |
| 5,546,945 | A | 8/1996 | Soldner |
| 5,553,111 | A | 9/1996 | Moore |
| 5,603,326 | A | 2/1997 | Richter |
| 5,640,956 | A | 6/1997 | Getzinger et al. |
| 5,662,109 | A | 9/1997 | Hutson |
| 5,664,573 | A | 9/1997 | Shmulewitz |
| 5,706,327 | A | 1/1998 | Adamkowski |
| 5,709,206 | A | 1/1998 | Teboul |
| 5,719,398 | A | 2/1998 | Colak |
| 5,803,082 | A | 9/1998 | Stapleton et al. |
| 5,830,141 | A | 11/1998 | Makram-Ebeid et al. |
| 5,839,441 | A | 11/1998 | Steinberg |
| 5,840,022 | A | 11/1998 | Richter |
| 5,851,180 | A | 12/1998 | Crosby |
| 5,855,554 | A | 1/1999 | Schneider et al. |
| 5,883,937 | A | 3/1999 | Schmitt |
| 5,910,119 | A | 6/1999 | Lin |
| 5,933,518 | A | 8/1999 | Cohen-Solal |
| 5,938,613 | A | 8/1999 | Shmulewitz |
| 5,984,870 | A | 11/1999 | Giger et al. |
| 6,027,457 | A | 2/2000 | Shmulewitz |
| 6,064,715 | A | 5/2000 | Sklebitz et al. |
| 6,106,471 | A | 8/2000 | Wiesauer et al. |
| 6,117,080 | A | 9/2000 | Schwartz |
| 6,128,523 | A | 10/2000 | Bechtold et al. |
| 6,186,949 | B1 | 2/2001 | Hatfield et al. |
| 6,248,071 | B1 | 6/2001 | Lin |
| 6,254,538 | B1 | 7/2001 | Downey et al. |
| 6,310,477 | B1 | 10/2001 | Schneider |
| 6,317,617 | B1 | 11/2001 | Gilhuijs et al. |
| 6,336,082 | B1 | 1/2002 | Nguyen et al. |
| 6,409,668 | B1 | 6/2002 | Wollschlaeger |
| 6,421,454 | B1 | 7/2002 | Burke et al. |
| 6,432,053 | B1 | 8/2002 | Fecht et al. |
| 6,442,290 | B1 | 8/2002 | Ellis et al. |
| 6,450,962 | B1 | 9/2002 | Brandl et al. |
| 6,478,739 | B1 | 11/2002 | Hong |
| 6,482,158 | B2 | 11/2002 | Mault |
| 6,482,159 | B1 | 11/2002 | Wiesauer et al. |
| 6,514,618 | B1 | 2/2003 | McKeighen |
| 6,520,915 | B1 | 2/2003 | Lin et al. |
| 6,524,247 | B2 | 2/2003 | Zhao et al. |
| 6,524,252 | B1 | 2/2003 | Yu et al. |
| 6,529,766 | B1 | 3/2003 | Guendel |
| 6,574,499 | B1 * | 6/2003 | Dines et al. .................. 600/427 |
| 6,682,484 | B1 | 1/2004 | Entrekin |
| 6,846,289 | B2 | 1/2005 | Besson |
| 2001/0044581 | A1 | 11/2001 | Mault |
| 2001/0048440 | A1 | 12/2001 | Wiesauer |
| 2002/0156376 | A1 | 10/2002 | Wang et al. |
| 2002/0173719 | A1 | 11/2002 | Zhao et al. |
| 2002/0173722 | A1 | 11/2002 | Hoctor et al. |
| 2002/0188198 | A1 | 12/2002 | Hong |
| 2003/0007598 | A1 | 1/2003 | Wang et al. |
| 2004/0039285 | A1 | 2/2004 | Ustuner |

FOREIGN PATENT DOCUMENTS

| | | |
|---|---|---|
| EP | 1195901 | 4/2002 |
| WO | 0154583 | 8/2001 |
| WO | 0188682 | 11/2001 |
| WO | 0241751 | 5/2002 |
| WO | 0241752 | 5/2002 |
| WO | 0243801 | 6/2002 |
| WO | 0247533 | 6/2002 |
| WO | 02075578 | 9/2002 |
| WO | 02091906 | 11/2002 |

* cited by examiner

ULTRASOUND IMAGING SYSTEM WITH PIVOTING BREAST COMPRESSION PLATES

RELATED APPLICATIONS

This application is a continuation of U.S. patent application Ser. No. 10/616,319, entitled "Ultrasound Breast Screening Device," filed Jul. 9, 2003, now U.S. Pat. No. 7,806,827, which, in turn, claims the benefit of U.S. Provisional Application No. 60/453,644, filed Mar. 11, 2003, entitled "Integrated Auto-Scan, Full Field 3D Ultrasound Breast Screening Device," both of which are hereby expressly incorporated by reference in their entireties.

BACKGROUND OF THE INVENTION

Embodiments of the present invention generally relate to ultrasound breast screening systems, and more particularly to ultrasound breast screening systems having automated ultrasound transducers positioned on at least one compression plate.

Typically, x-ray mammography is used as the primary screening procedure for detection of breast lesions. For each x-ray mammogram screening of a patient, a top view, referred to as a cranio-caudal view ("CC" view), and a mediolateral oblique view ("MLO" view) are usually taken.

X-ray mammography, however, poses various patient comfort issues. For example, a patient's breast is typically compressed during a mammographic procedure. The force of the compression, and the orientation of the compressing members, may cause pain and overall discomfort. Additionally, x-ray mammography may be hazardous due to the fact that x-ray mammography uses ionizing radiation. Further, studies have shown that mammography generates false positives in more than 10% of patients and that that x-ray mammography is not always effective and accurate with respect to dense breasted women because lesions masked by dense breast tissue may go undetected.

Sonography, or ultrasound, has been used as a complementary screening procedure to confirm screening results. In fact, sonography has gained acceptance as a viable alternative to x-ray mammography for breast imaging, due to the drawbacks and hazards associated with x-ray mammography. For example, sonography has been used when X-ray mammography has failed to confirm the results of a manual examination.

When sonography is used in conjunction with x-ray mammography, the rate of accurate detection of lesions improves to over 90%. However, two separate imaging procedures, that is, x-ray mammography and ultrasound breast imaging, are required for a single patient, which is inconvenient and may even delay diagnosis. Further, the dual use of x-ray mammography and ultrasound breast imaging requires skilled specialists and typically at least twenty minutes of screening time.

Hand-held ultrasound transducer probes have been used in examinations to complement X-ray mammography. A drawback of such freehand examinations, when used to supplement mammography, is the inability to provide geometric registration between the mammogram and ultrasound images. The lack of registration makes it difficult to relate what is seen in the ultrasound image to what is seen in the mammogram. Furthermore, the three dimensional shape of the lesions and the increased vascularity associated with carcinoma make volumetric spatial registration of the ultrasonic data with a mammogram desirable.

U.S. Pat. No. 5,479,927, issued to Shmulewitz, entitled "Methods and Apparatus for Performing Sonomammography and Enhanced X-Ray Imaging," (the "'927 patent") which is hereby expressly incorporated herein in its entirety, describes a system that combines mammography equipment with an ultrasound transducer to generate ultrasonic images of the internal structure of breast tissue that are in geometric registration with a mammographic image. The system disclosed in the '927 patent includes a radiolucent and sonolucent compression plate. Either before or after the x-ray exposure, a carriage-mounted ultrasound transducer is translated in increments across the compression plate to generate a plurality of sectional views of the breast tissue. The x-ray and ultrasound images produced by this sonomammography apparatus are ideally in geometric registration. Those images may in turn be processed by a conventional microprocessor-based workstation to provide holographic views of the internal features of a patient's breast.

X-ray mammography images are typically obtained using a plastic plate to compress the breast. The compression plates used in x-ray mammography were historically made of polycarbonates, which are acoustically opaque, because of their tensile strength and transparency to x-ray. Most other materials potentially useful for the compression plates in mammography equipment have relatively high densities and thus exhibit relatively high attenuation and reflection coefficients for acoustic wave energy. The '927 patent discloses a compression plate made of a high-performance acoustically transparent (sonolucent) and x-ray transparent (radiolucent) film that is sufficiently rigid to serve as a compression plate at a thickness of about 25 micron (1 mil).

As shown in the '927 patent, however, a breast is compressed between two compressive members that are parallel with one another, and typically parallel with the plane of the floor. The compressive members move toward each other to compress the breast. The breast typically needs to be substantially flattened between the plates so that the plates may be in proper contact with the breast for imaging. A certain force, which may vary among patients, is used to substantially flatten the breast between the two parallel plates so that proper contact is obtained with substantially the entire breast. However, the force needed to properly flatten the breast often causes the patient pain and discomfort.

U.S. Patent Application 2003/0007598, filed May 31, 2002, entitled "Breast Cancer Screening With Adjunctive Ultrasound Mammography," (the "'598 application") which is hereby expressly incorporated herein in its entirety, discloses systems and methods for intuitive viewing of adjunctive ultrasound data concurrently with x-ray mammogram information. Instead of registering the ultrasound images with the x-ray images, the '598 application teaches displaying "thick" slice images near an x-ray mammogram so that a screening radiologist may quickly view the thick slice images for assistance in interpreting the x-ray mammogram.

U.S. Application No. 2002/0173722, filed Apr. 5, 2001, entitled "Focus Correction for Ultrasound Imaging Through Mammography Compression Plate," (the "'722 application"), which is hereby expressly incorporated herein in its entirety, describes an ultrasound imaging system capable of acquiring an image of a tissue through a plastic plate. The '722 application discloses a beamformer that is programmed with pre-stored transmit and receive time delays that are computed to correct the effects of refraction caused by an intervening plastic mammography compression plate of an x-ray mammography system. The correction enables acquisition of an in-focus ultrasound image taken under the same conditions as an x-ray mammography compression image. As disclosed in the '722 application, because the ultrasound and x-ray mammography images are formed from the same source under the same conditions, the images may be registered.

Conventional ultrasound imaging systems comprise an array of ultrasonic transducer elements that transmit an ultrasound beam and receive the reflected beam from the object being studied. After a focused ultrasound wave is transmitted, the system switches to receive mode after a short time interval, and the reflected ultrasound wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasound waves are received.

An ultrasound array typically has a plurality of transducer elements arranged in one or more rows. The elements are usually driven with separate voltages. By selecting the time delay (or phase) and amplitude of the applied voltages, the individual transducer elements in a given row may be controlled to produce ultrasonic waves that combine to form a net ultrasonic wave that travels along a preferred beam vector direction and is focused at a selected point along the beam. The beamforming parameters of each of the firings may be varied to provide a change in maximum focus or otherwise change the content of the received data for each firing, for example, by transmitting successive beams along the same scan line with the focal point of each beam being shifted relative to the focal point of the previous beam. For a steered array, by changing the time delays and amplitudes of the applied voltages, the beam with its focal point may be moved in a plane to scan the object.

The same principles apply when the transducer probe is employed to receive the reflected sound in a receive mode. The voltages produced at the receiving transducer elements are summed so that the net signal is indicative of the ultrasound energy reflected from the object. As with the transmission mode, the focused reception of the ultrasonic energy is achieved by imparting separate time delay (and/or phase shifts) and gains to the signal from each receiving transducer element.

Figure 1:
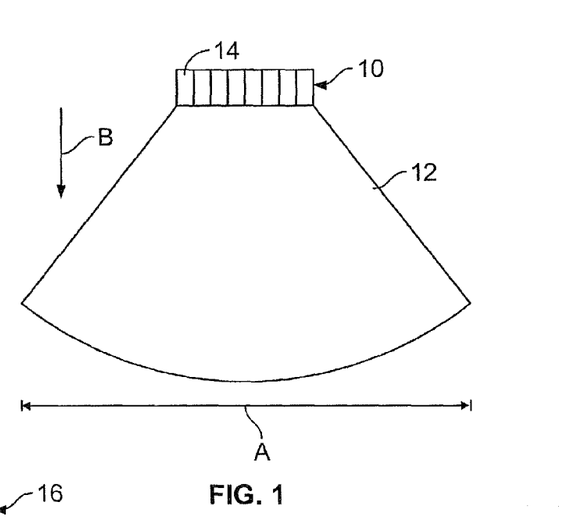
FIG. 1 illustrates a conventional sector array that may be used with an ultrasound probe.

FIG. 1 illustrates a conventional sector array 10 that may be used with an ultrasound probe. For the sake of clarity, the ultrasound probe is not shown. Rather, only the sector array 10 and field of view 12 are shown. The sector array 10 includes a plurality of ultrasound elements 14. As shown in FIG. 1, the sector array 10 transmits and receives ultrasound waves over a wide field of view 12 by applying appropriate time delay to steer the ultrasound beam. The width A of the field of view 12 is wider than that of a linear array, as shown below with respect to FIG. 2. However, the imaging resolution of the sector array 10 decreases with increased depth in the direction of line B.

Figure 2:
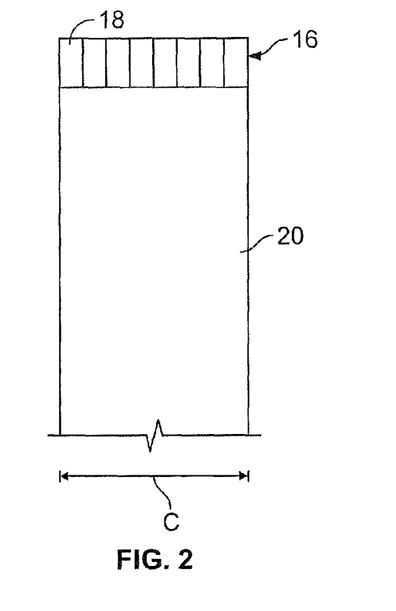
FIG. 2 illustrates a conventional linear array that may be used with an ultrasound probe.

FIG. 2 illustrates a conventional linear array 16 that may be used with an ultrasound probe. Similar to the sector array 10, the linear array 16 includes a plurality of ultrasound elements 18. As shown in FIG. 2, the linear array 16 transmits and receives ultrasound waves over a relatively narrow field of view 20, as compared to that of the sector array 10 due to limited steering capabilities of linear probes. That is, the width C of the field of view 20 of the linear array is not as wide as the width A of the field of view 12 of the sector array 10, as shown in FIG. 1. However, while the linear array 16 exhibits a relatively narrow field of view 20, the imaging resolution of the linear array 16 is uniform throughout the field of view 20.

Figure 3:
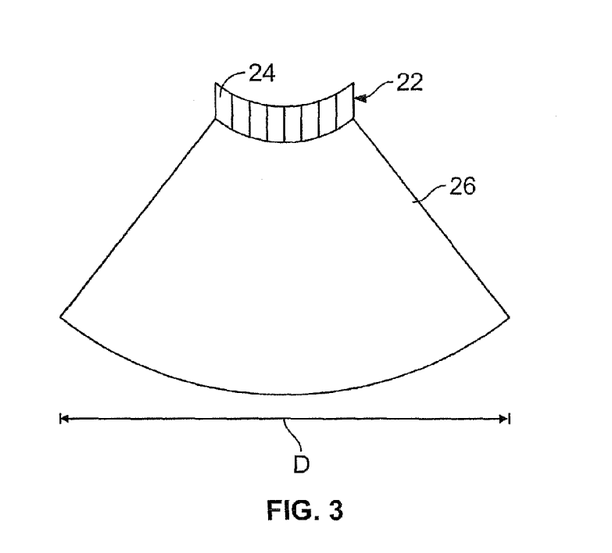
FIG. 3 illustrates a conventional curved array that may be used with an ultrasound probe.

FIG. 3 illustrates a conventional curved array 22 that may be used with an ultrasound probe. The curved array 22 is defined by a plurality of ultrasound elements 24. Similar to the linear array 16 shown in FIG. 2, the curved array 22 has limited steering capabilities. A wider field of view is obtained by shaping the array in a curved format. The curved array 22 is a hybrid of the sector array 10 and the linear array 16 in that it is designed to transmit and receive ultrasound waves over a wider field of view 26, as compared to the liner array 16, while maintaining a more uniform imaging resolution throughout the field of view 26 as compared to the sector array 10. The width D of the field of view 12 of the curved array 22 is wider than that of the linear array 16.

In conventional ultrasound probes, such as linear, sector and curved array probes, when an ultrasound beam is electronically steered off center, the ultrasound beam tends to widen. The corresponding reflected ultrasound beam reflects off an area of such a size that the data is typically "volume averaged" in order to construct an image. However, volume averaging may mask structures within a piece of anatomy, due to the fact that the image includes, in effect, estimates of the anatomical structure.

Conventional ultrasound probes, having sector, linear or curved arrays, use a single row of transducer elements, as discussed above with respect to FIG. 1-3. As is well known, using a single row of elements limits the focusing ability of the transducer elements in the near and far fields. Consequently, pathologies may be masked due to volume averaging techniques required to focus in the near and far fields.

Thus, a need exists for a more patient-friendly ultrasound breast imaging system. A need also exists for an ultrasound breast imaging system that automatically scans a patient's breast with more clarity and accuracy.

SUMMARY OF THE INVENTION

Embodiments of the present invention provide a breast imaging and display system that includes a central processing unit (CPU), an imaging workstation in electrical communication with the CPU, and an ultrasound breast imaging assembly operatively connected to, and in electrical communication with, the CPU. The ultrasound breast imaging assembly includes upper and lower compression plates, a breast compression area defined between the upper and lower compression plates, at least one pivot assembly, and an ultrasound probe.

The pivot assembly allows relative motion between the upper and lower compression plates while the planes of said upper and lower compression plates are angled with respect to one another. The pivot assembly may be operatively connected to at least one of the upper and lower compression plates. One of the upper and lower compression plates may remain in a fixed orientation with respect to the other before and during the relative motion between the two. The pivot assembly may comprise a spring member that connects said upper compression plate to said lower compression plate, providing compressive forces therebetween.

The ultrasound breast imaging assembly also includes an upright member supported by a base. One of the upper and lower compression plates includes a sonolucent compression film, while the other includes a sound absorbing stabilization plate. The upper compression member may be operatively connected to an upper pivot assembly, which may in turn be connected to an upper extension member, which may in turn be translationally secured to the upright member. Similarly, the lower compression member may be operatively connected to a lower pivot assembly, which may in turn be connected to a lower extension member, which may in turn be translationally secured to the upright member. Both the upper and lower extension members may be perpendicular to the upright member. The upper and lower extension members may translate over the upright member. A swivel member may connect the pivot assembly and upper and lower compression plates to the upright member. The swivel member is configured to rotate the upper and lower compression plates through a plurality of imaging orientations, including craniocaudal (CC) and mediolateral oblique (MLO) orientations.

While the compression plates move with respect to one another, the angle between the compression plates changes. The movement between the compression plates may be arcuate, pivotal movement. During movement, the compression plates are not parallel with one another. The upper and lower compression plates are configured to adequately contact the breast for imaging even though the breast is not substantially flattened.

The ultrasound probe includes an active matrix array (AMA) positioned on one of the upper and lower compression plates. The ultrasound probe is configured to translate over one of the upper and lower compression plates. The AMA comprises a plurality of rows having a plurality of ultrasound elements. At least one group or subset of the ultrasound elements is selectively activated and deactivated during an imaging procedure The ultrasound breast imaging assembly may also be used with an x-ray mammography system. For example, the ultrasound breast imaging assembly may be secured to a portion of the x-ray mammography system.

The CPU receives image data from the ultrasound probe and automatically analyzes the image data for lesions, cysts and microcalcifications. The CPU displays an ultrasound image, which is derived from the ultrasound probe imaging a breast, on a monitor of the image workstation. The CPU may also display an x-ray mammographic image on the monitor within close proximity of the ultrasound image. The ultrasound image may be registered with the x-ray mammographic image. The ultrasound image may be a representation of an individual ultrasound slice, or a thick slice that includes a plurality of individual ultrasound slices stacked on top of one another. The CPU may also display a CINE loop of individual ultrasound slices on the monitor.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

Figure 15:
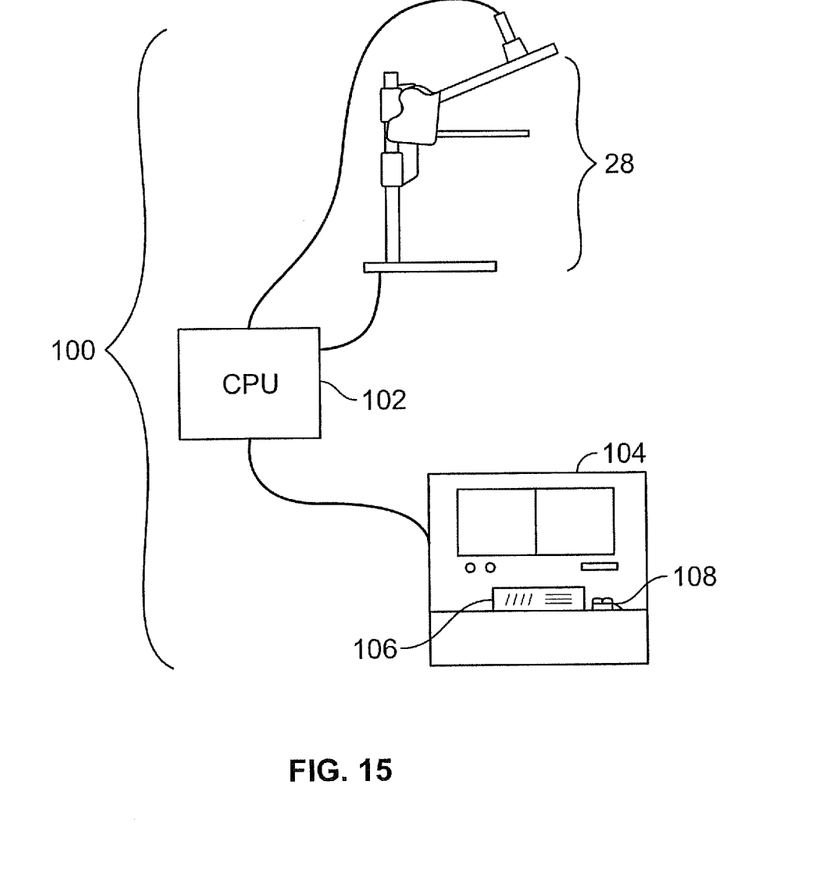
FIG. 15 is a schematic diagram of an ultrasound imaging system according to an embodiment of the present invention.

FIG. 15 is a schematic diagram of an ultrasound imaging system 100 according to an embodiment of the present invention. The ultrasound imaging system 100 includes an ultrasound imaging device 28, which is in electrical communication with a central processing unit (CPU) 102. The CPU 102 may control movement of an imaging transducer (discussed below) and the movement of compression plates (discussed below) of the ultrasound imaging device 28. The CPU 102 sends control commands to the ultrasound imaging device 28, and receives data signals from the ultrasound imaging device 28. The CPU 102 analyzes the data signals received from the ultrasound imaging device in order to form images for display. The CPU 102 is also in electrical communication with an imaging workstation 104, which displays image data received from the CPU 102. That is, the CPU 102 may send signals to, and receive signals from, the imaging workstation 104. A user may enter imaging and display commands through input devices, such as a keyboard 106 and/or a mouse 108 at the imaging workstation 104.

Figure 4:
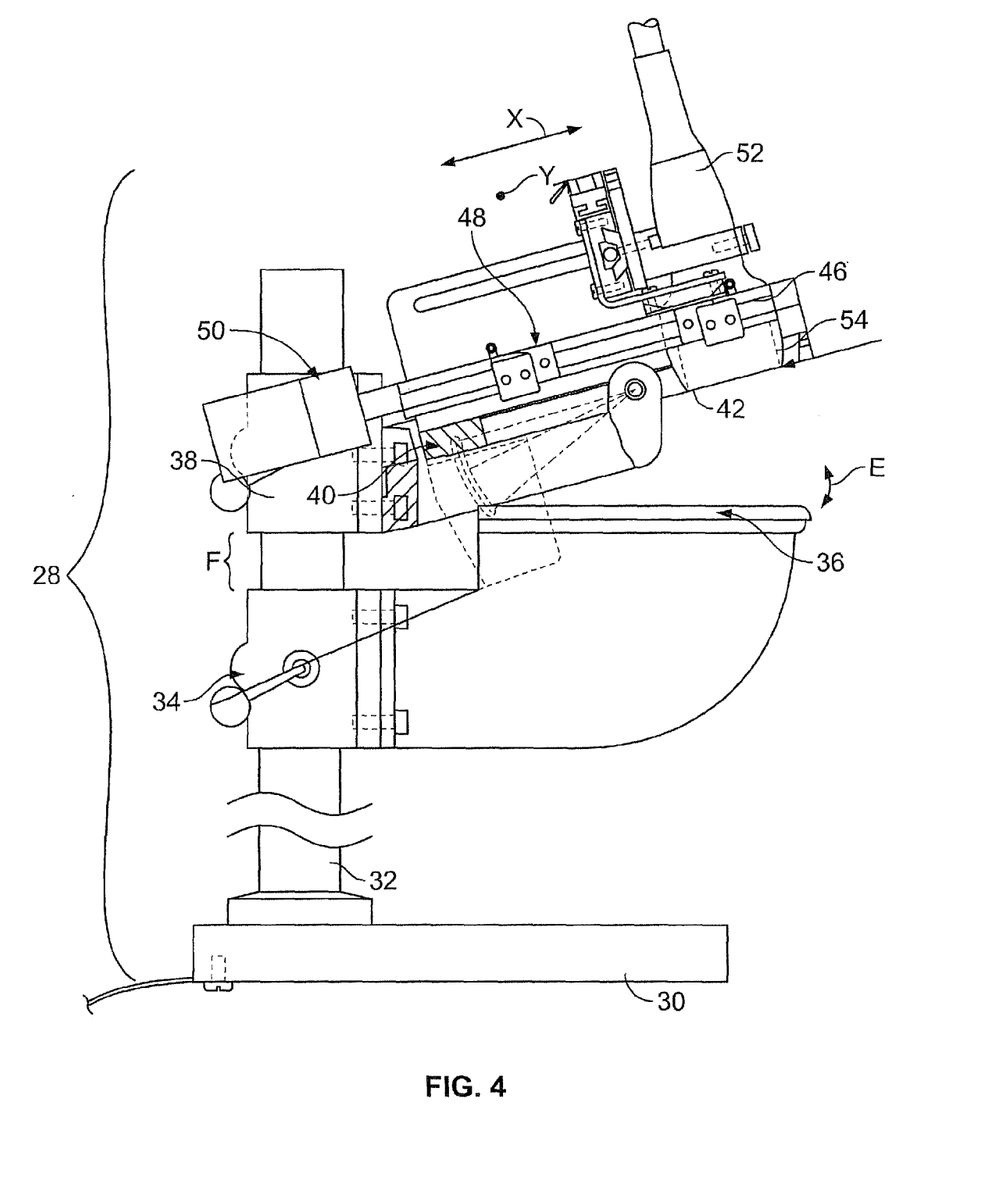
FIG. 4 illustrates a side view of a breast imaging device according to an embodiment of the present invention.

FIG. 4 illustrates a side view of the ultrasound breast imaging assembly 28. The ultrasound breast imaging assembly 28 may be used in conjunction with an x-ray mammography system, such as shown in the '927 patent and the '722 application. Additionally, the breast imaging device 28 may be used with a computer network, a server, and a screening station, similar to that shown in the '598 application.

The ultrasound breast imaging assembly 28 includes a base 30 that is connected to, or integrally formed with, an upright member 32. The upright member 32 includes a lower adjusting bracket 34 that may assist in supporting a lower compression plate 36 that includes a sound absorbing bottom breast stabilization plate.

An upper adjusting bracket 38 is also positioned on the upright member 32 above the lower adjusting bracket 34. As shown in FIG. 4, the upper adjusting bracket 38 is positioned a distance F above the lower adjusting bracket 34. The distance F may be greater or less than that shown in FIG. 4. For example, the upper adjusting bracket 38 may be directly adjacent the lower adjusting bracket 34, thereby minimizing the distance F. The upper adjusting bracket 38 may assist in supporting an upper compression plate 40 that includes an upper breast stabilization plate, or frame. The upper compression plate supports and frames a sonolucent (i.e., acoustically transparent) compression film 42. The sonolucent compression film 42 is sufficiently rigid to serve as a compressive member. That is, a breast may be sandwiched between the sonolucent compression film 42 and the lower compression plate 36 without compromising the structural integrity of the sonolucent compression film 42. The sonolucent compression film 42 and the lower compression plate 36 may also be radiolucent (i.e., X-ray transparent), as described in the '927 patent.

The upper compression plate 40 also includes a probe translation assembly 46 mounted above the sonolucent compression film 42. The probe translation assembly 46 includes a system of longitudinal and lateral rails 48 operatively connected to a motor 50 and a transducer, or probe, 52 having a probe head 54. The system of longitudinal and lateral rails 48 are aligned parallel to the plane of the sonolucent compression film 42. The motor 50 is used to actuate the probe 52 in the x-direction and/or the y-direction. The probe 52 may transmit and receive ultrasound signals through the sonolucent compression film 42. The probe translation assembly 46 may be configured so that the probe 52 moves over the sonolucent compression film similar to the movement described by the transducer and gantry system shown and described in the '927 patent. The probe translation assembly 46 and the probe 52 are controlled by the CPU 102. Optionally, the probe 52 may translate over the sonolucent compression film 42 through various systems, such as pulleys, worm-screws, cogs and wheels, and the like.

As noted above, the lower compression plate 36 includes a sound absorbing breast stabilization plate and the upper compression plate 40 includes the probe translation assembly 46 and the sonolucent compression film 42. Alternatively, the lower compression plate 36 may include the sonolucent compression film and a probe translation assembly on a lower surface thereof, while the upper compression plate may be configured to include a sound absorbing stabilization plate.

Figure 5:
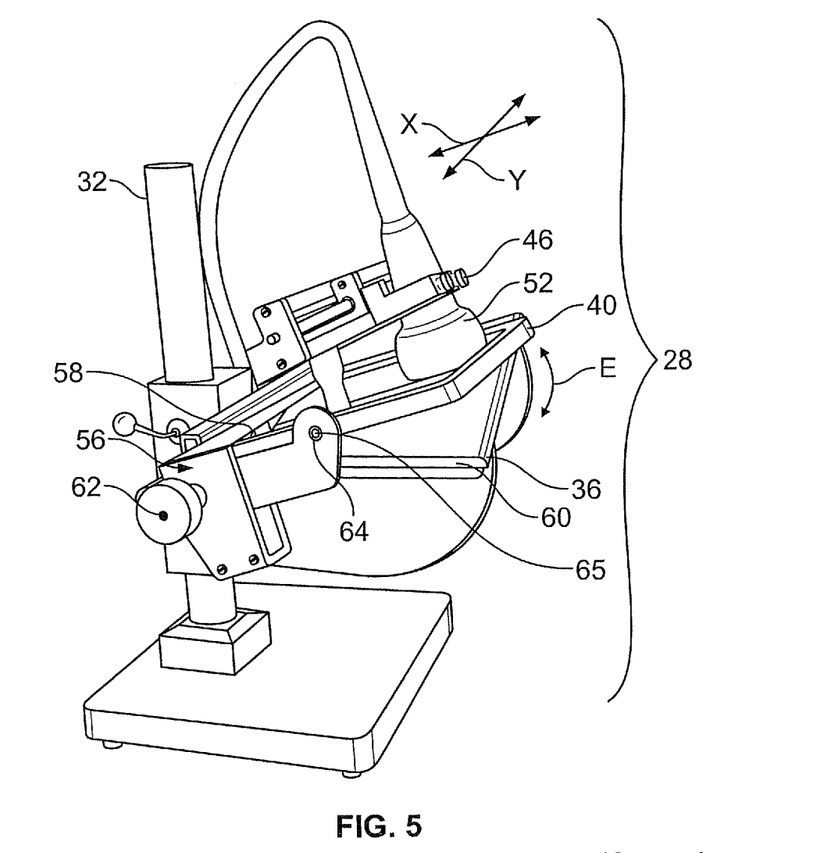
FIG. 5 illustrates an isometric upper view of an ultrasound breast imaging assembly according to an embodiment of the present invention.

FIG. 5 illustrates an isometric upper view of the ultrasound breast imaging assembly 28. The upper compression plate 40 is pivotally connected to a pivot assembly 56. The pivot assembly 56 may include upper guide tracks (not shown) that securably retain portions of lateral edges 58 of an end of the upper compression plate 40. Additionally, the pivot assembly 56 may include lower guide tracks (not shown) that securably retain portions of lateral edges 60 of an end of the lower compression plate 36. The pivot assembly 56 is configured to pivot or otherwise move the upper compression plate 40 with respect to the lower compression plate 36, or vice versa, over an arcuate path in the direction of arc E about a axis 62 that extends axially through the pivot assembly 56. Alternatively, the lower compression plate 36 may not be connected to the pivot assembly 56. Instead, the lower compression plate 36 may be secured to the upright member 32 in a fixed position, while the upper compression plate 40 moves with respect to the lower compression plate 36 in the direction of arc E by way of pivotal movement about the axis 62. Also, optionally, the lower compression plate 36 may be connected to the pivot assembly 56, but its downward movement may be impeded by a structure on the ultrasound breast imaging assembly 28. In this case, the upper compression plate 40 may move in the direction of arc E toward the lower compression plate 36, which remains in a fixed orientation.

Figure 6:
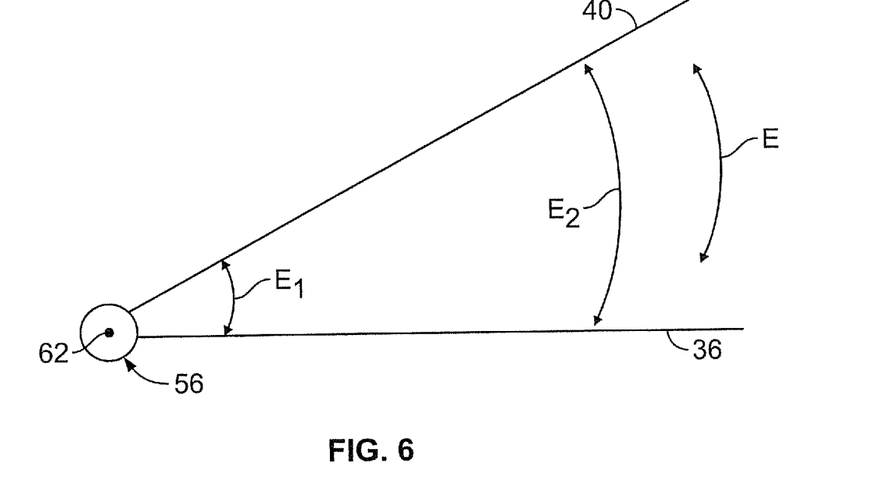
FIG. 6 illustrates a simplified representation of a pivot assembly according to an embodiment of the present invention.

FIG. 6 illustrates a simplified representation of the pivot assembly 56. As shown in FIG. 6, the upper compression plate 40 may move toward the lower compression plate 36, or vice versa, in the direction of arc E by pivoting about the axis 62 with respect to the lower compression plate 36. The axis 62 may include a rotating rod, hinge, or the like, that allows pivotal movement between the upper compression plate 40 and the lower compression plate 36. Optionally, the axis 62 may remain in a static, fixed position, while each of the compression plates 36 and 40 include a loop member or other such feature at an end proximate the rod that rotatably secures the compression plates 36 and 40 to the rod. Also, optionally, the axis 62 may include ball bearing members that are coaxially aligned with the rod that operatively connect to the compression plates 36 and 40, respectively, thereby allowing each of the compression plates to independently rotate about the rod. As mentioned above, the lower compression plate 36 may not be connected to the pivot assembly 56. Rather, the lower compression plate may be in a fixed position, or may be connected to an additional pivot assembly (not shown) that is distinct from the pivot assembly 56. Also, alternatively, the upper compression plate 40 may be in a fixed position while the lower compression plate 36 moves with respect to the upper compression plate 40 in the direction of arc E. Overall, the pivot assembly 56 is configured to allow at least one of the compression plates 36 and 40 to pivot thereon and move toward the counterpart compression plate in the direction of arc E.

Referring again to FIG. 5, the movement of the compression plates 36 and 40 with respect to one another in the direction of arc E may be controlled by a central processing unit, such as the CPU 102, or a computer network. Optionally, the compression plates 36 and 40 may be manually moved in the direction of arc E with respect to one another. The pivot assembly 56 may also include braking members that secure the compression plates 36 and 40 with respect to one another in the direction of arc E.

The top compression plate 40 may also pivot with respect to an axis 65 defined by fasteners 64 that assist in securing the probe translation assembly 46 to the top compression plate 40. One fastener 64 may be pivotally secured into one lateral edge 58 while another fastener 64 may be pivotally secured into the other lateral edge 58. Thus, the top compression plate 40 may be pivotally positioned with respect to the axis 65 in addition to being able to pivot about the axis 62 in the direction of arc E. Similarly, the lower compression plate 36 may also be configured to pivot with respect to an axis (not shown) that is distinct from the axis 65.

Figure 7:
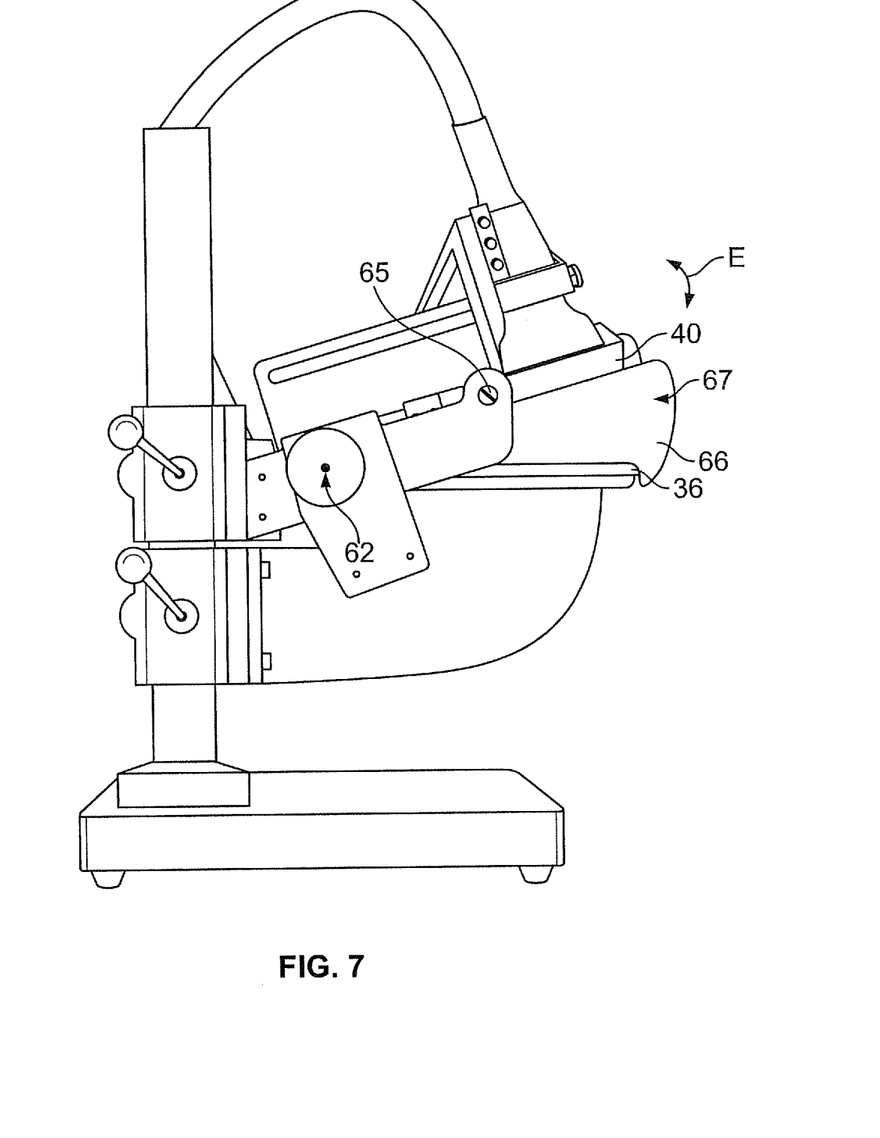
FIG. 7 illustrates a side view of a breast imaging device during an imaging procedure according to an embodiment of the present invention.

FIG. 7 illustrates a side view of the breast imaging device 28 during an imaging procedure. As shown in FIG. 7, an object representing a breast 66 is positioned within a breast compression area 67, defined between the compression plates 36 and 40. The compression plates 36 and 40 compress the breast 66 by pivoting or otherwise moving with respect to one another, as discussed above. For example, the upper compression plate 40 may be pivotally attached to, and pivot with respect to, the axis 62 while the lower compression plate 36 remains in a fixed orientation. Optionally, the lower compression plate 36 may be pivotally attached to, and pivot with respect to, the axis 62 while the upper compression plate 40 remains in a fixed orientation. Further, the upper compression plate 40 may pivot with respect to the axis 65 in order to better conform to the size and shape of the breast 66. Also, the lower compression plate 36 may pivot with respect to an axis that is distinct from the axes 62 and 65.

Overall, the configuration of the breast compression area of the ultrasound breast imaging assembly 28 is anatomically closer to the size and shape of a breast as compared to that of two parallel compression plates that compress a breast. As shown above, the compression plates 36 and 40 are angled with respect to one another. At all positions along a range of motion, the compression plates 36 and 40 remain angled with respect to one another. That is, the planes of the compression plates 36 and 40 are not parallel to one another. Thus, less compressive force is needed to compress the breast 66 as compared to systems using parallel plate compression. Because the compression plates 36 and 40 are angled with respect to one another, the compression plates 36 and 40 may conform to the shape and size of a particular breast, by way of pivotal compression. Because the compression plates 36 and 40 compress the breast 66 in a pivoting fashion over an arcuate path, a smaller clearance area exists between the compression plates 36 and 40 at a distal area of the breast (such as the nipple), where the breast is smaller, than at a proximate area of the breast (such as by the chest wall), where the breast is wider and thicker. For example, as shown in FIG. 6, the range of motion between the compression plates 36 and 40 is smaller at $E_1$ as compared to $E_2$. Thus, less force is required to compress the breast (as compared to prior systems such as that described in the '927 patent) due to the fact that the compression plates 36 and 40 are configured to better conform to the general shape of the breast 66. The breast 66 does not have to be substantially flattened in order for the compression plates 36 and 40 to properly contact and compress the breast for imaging.

Figure 8:
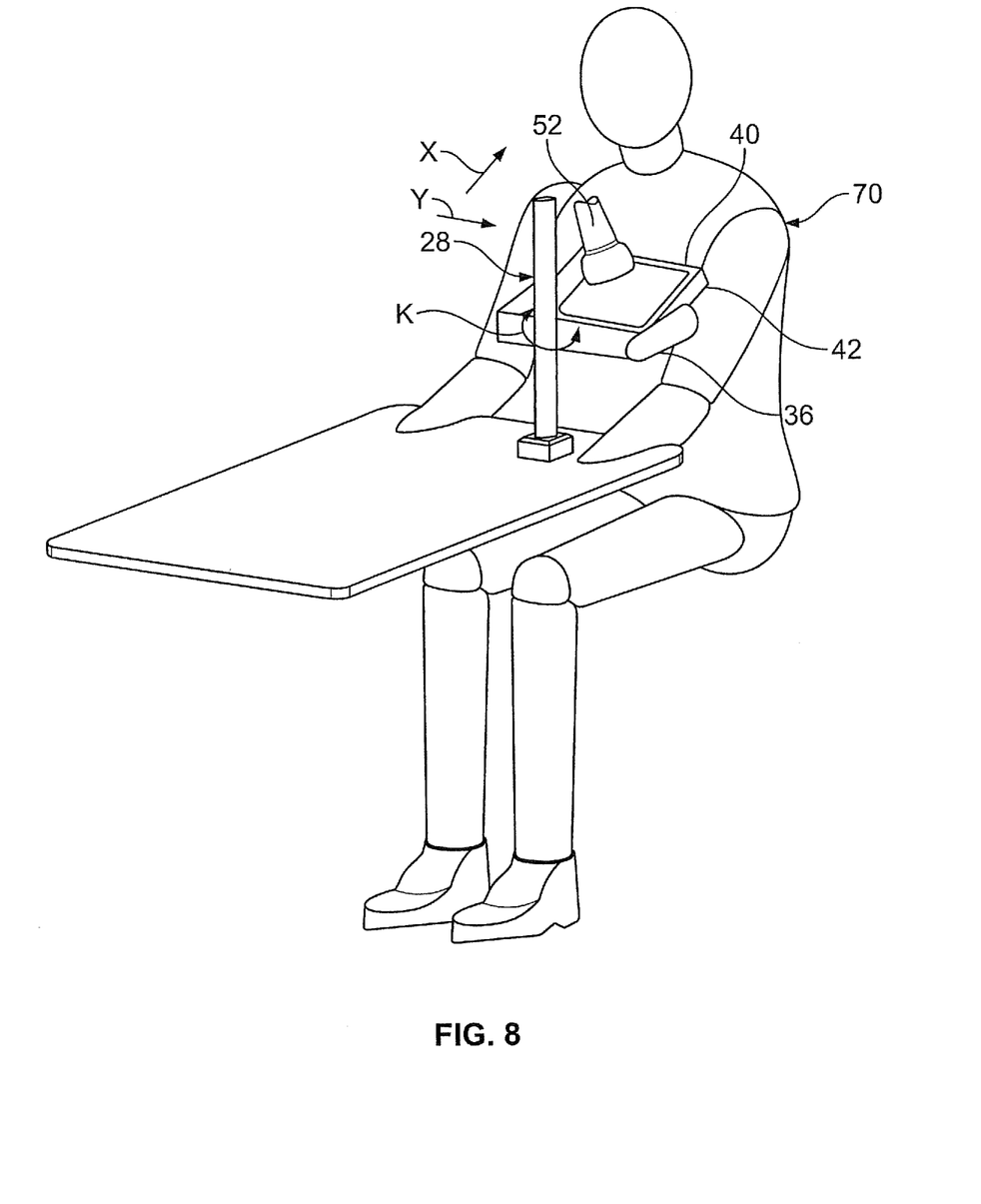
FIG. 8 illustrates an isometric view of a patient being imaged by a breast imaging device according to an embodiment of the present invention.

FIG. 8 illustrates an isometric view of a patient 70 being imaged by the ultrasound breast imaging assembly 28. The patient 70 is being imaged in the "standard" mammography position. That is, the patient is positioned in a manner that is similar to an imaging position in an x-ray mammography procedure in which the resulting view is a CC view. When the patient 70 is imaged in the standard CC view, each individual ultrasound slice is computed directly from an acquired ultrasound image or ultrasound frame. In order to image the breast of the patient 70 in a different orientation, or to display different views of the breast, the ultrasound slices may be combined to form a 3D representation of the breast, with various cross sectional views from various angles of the 3D representation being displayed on a monitor, or other such display, of an imaging workstation, such as the imaging workstation 104 of FIG. 15. The ultrasound data is received by a central processing unit, such as CPU 102, which in turn analyzes the data, and performs various reconstruction algorithms with respect to the data received from the probe in order to display the data on the imaging workstation 104.

The compression plates 36 and 40 may be directly or indirectly connected to a swiveling member (as discussed below with respect to FIG. 9) that allows the compression plates 36 and 40 to rotate about an axis in the K direction. Thus, the compression plates 36 and 40 may be oriented to compress the breast for imaging in the MLO view and other orientations.

As shown in FIG. 8, the ultrasound breast imaging assembly 28 is supported by a table type structure. Alternatively, the ultrasound breast imaging assembly may be mounted to an x-ray mammography imaging system in a similar fashion as shown in the '927 patent.

Figure 9:
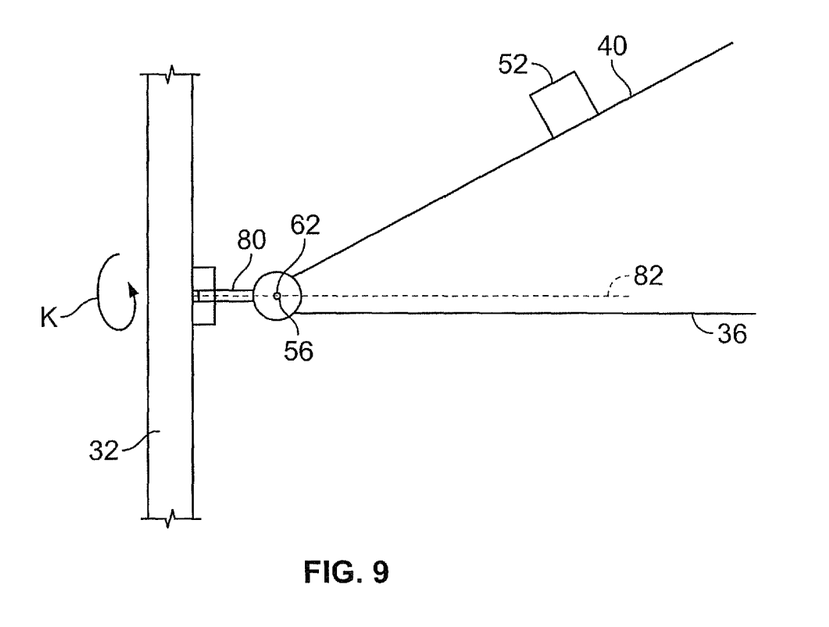
FIG. 9 illustrates a simplified side view of a breast imaging device according to an alternative embodiment of the present invention.

FIG. 9 illustrates a simplified side view of the ultrasound breast imaging assembly 28 according to an alternative embodiment of the present invention. The pivot assembly 56 may be connected to a swiveling member 80 that is secured to the upright member 32. The swiveling member 80 may rotate the pivot assembly 56 and the compression plates 36 and 40 through the K direction with respect to an axis 82. As shown in FIG. 9, the axis 82 is disposed within the same horizontal plane as, but perpendicular to, the axis 62. Thus, the compression plates 36 and 40 may be positioned to image a breast through various angles and orientations.

Referring again to FIG. 8, for example, and as mentioned above, the probe 52 may translate over the sonolucent compression film 42 through the X and Y directions. That is, the probe 52 may move over substantially the entire area of the sonolucent compression film 42, which in turn, overlays an entire breast. Consequently, the probe 52 may sweep over and image the entire breast by way of the probe 52 translating over the sonolucent compression film 42 in the X and Y directions. The CPU 102 (shown in FIG. 15) may control the movement of the probe 52 in order to effectively image the entire breast. Thus, the ultrasound beams do not have to be steered a great extent to image distant portions of the breast because the probe 52 may be moved to desired positions over the breast. Further, as discussed below, the use of an active matrix array with the probe 52 may also minimize, if not obviate, beam steering.

Figure 10:
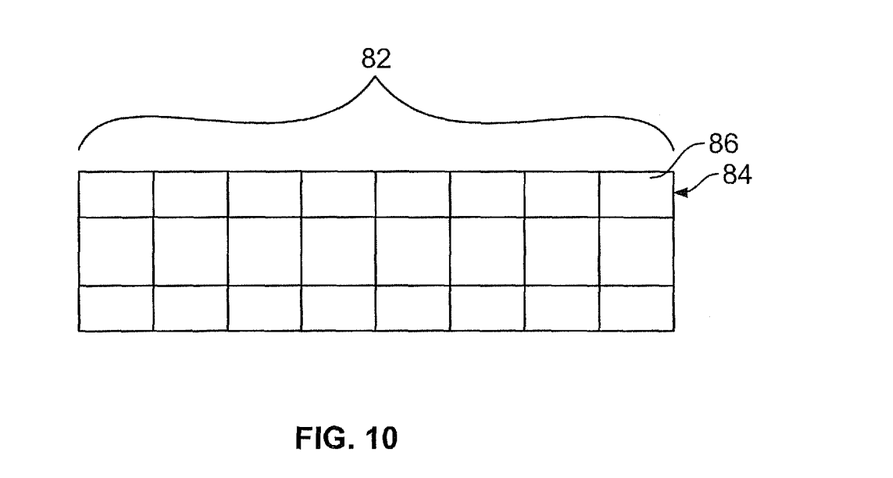
FIG. 10 illustrates an active matrix array (AMA) of an ultrasound probe according to an embodiment of the present invention.

FIG. 10 illustrates an active matrix array (AMA) 82 of the ultrasound probe 52 according to an embodiment of the present invention. The AMA 82 is positioned within the probe head 54 (shown, for example, in FIG. 4). The AMA 82 includes multiple rows 84 of ultrasound elements 86 that may be smaller than the ultrasound elements of sector, linear and curved arrays. While FIG. 10 shows three rows 84 of ultrasound elements 86, more or less rows may be used. Further, the size of the transducer elements 86 within adjacent rows 84 may also vary. For example, a first row of transducer elements 86 may be a first size, while a second row of transducer elements 86 may be a second size, and so on.

Increasing the number of rows 84 of ultrasound elements 86 increases an operator's control over the resolution of the transmitted and received ultrasound beams. Resolution increases (i.e., a narrower ultrasound beam is generated) with an increase in the number of active ultrasound elements 86 due to the fact that the multiple rows may be beamformed, thereby improving beam focus in the imaging direction. Thus, the volume of the breast that is intersected with an ultrasound beam is smaller and therefore, less volume averaging occurs when constructing an image. That is, the ultrasound beams reflect from a smaller area or volume, reducing the amount of volume averaging that occurs when constructing an image, thereby yielding a truer, more accurate image of the breast.

A probe, such as the probe 52, having the AMA 82 may control the resolution of the ultrasound beam across the scan plane. A probe using an AMA 82 allows control of the number of ultrasound elements 86. Groups of ultrasound elements 86 (e.g., certain rows, and/or portions of rows) are selectively activated and deactivated, that is, turned ON and OFF, as a breast is imaged. Thus, an AMA 82 may effectively control the width of the ultrasound beam as it scans through a scan plane, thereby keeping the width of the ultrasound beam relatively constant, resulting in a more uniform image.

The AMA 82 achieves uniform resolution throughout the entire field of view, significantly reducing volume averaging and improving diagnostic confidence. That is, the AMA 82 used in the probe 52 images the full field of the breast with minimal volume averaging in the resulting image. The probe 52 having the AMA 82 with multiple rows 84 of ultrasound elements 86 that are electronically scanned provides flexibility in imaging (i.e., how beams are created), additional gain, and better resolution. Embodiments of the present invention use a probe, such as the probe 52, having the AMA 82, which generates three dimensional (3D) images of the internal structure of a breast.

Figure 11:
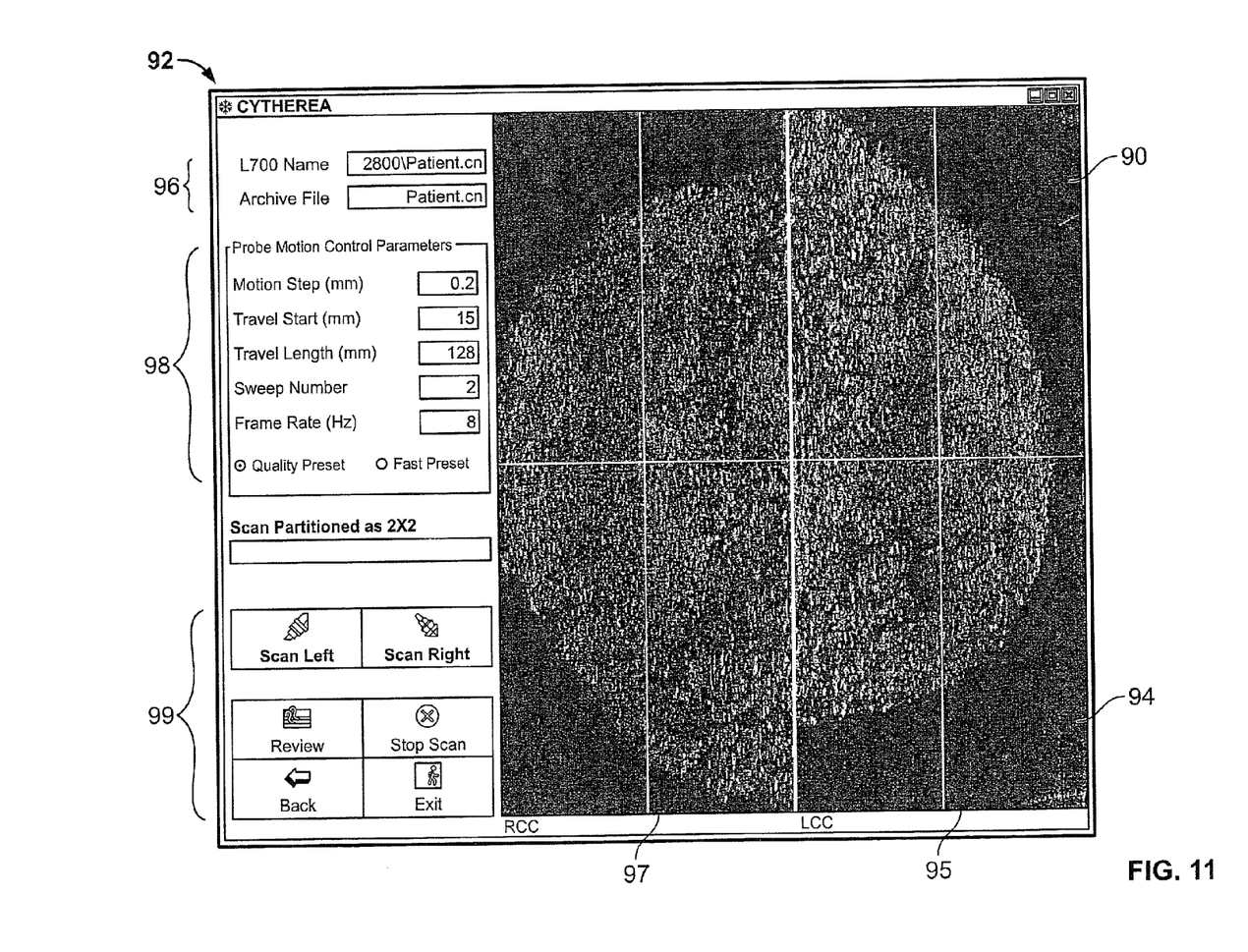
FIG. 11 illustrates a full-field ultrasound scan of a breast shown on a display of a breast imaging system according to an embodiment of the present invention.

FIG. 11 illustrates a full-field ultrasound scan 90 of a breast shown on a display 92 of a breast imaging system according to an embodiment of the present invention. The display 92 includes an image section 94, patient information 96, probe motion control parameters 98, and scan controls 99. The image section 94 shows a Right CC view 97 and a Left CC view 95. The images displayed are full-field images taken with an AMA probe. As shown in FIG. 11, the images displayed are ultrasound images shown in standard x-ray mammography orientations. Thus, the reviewing physician or technician may easily compare the images to corresponding x-ray mammography images.

Additionally, the images may be analyzed by a central processing unit, such as the CPU 102 shown in FIG. 15. The CPU 102 may apply computer aided detection (CAD) algorithms to the data received from the probe 52 to automatically detect lesions, cysts, microcalcifications and the like. The CPU 102 may include programs to examine architecture distortion common to cancers, detect increased blood flow, find masses among cysts, examine hardness of tissue and measure response to pressure. The CPU 102 may employ CAD techniques known in the art. For example, the CPU 102 of the system including the ultrasound breast imaging assembly 28 may use techniques described in U.S. Pat. No. 5,984,870, issued to Giger et al., entitled "Method and System for the Automated Analysis of Lesions in Ultrasound Images," which is hereby expressly incorporated by reference in its entirety.

The CPU 102 may display individual ultrasound slice images on a high resolution monitor of the imaging workstation 104. The individual ultrasound slice images may be displayed in a CINE loop on the display of the imaging workstation. The CPU 102 may also overlay a plurality of ultrasound slice images to form a "thick slice" image, which may then be displayed on the imaging workstation 104. The ultrasound images may be displayed on the imaging workstation 104 in conjunction with x-ray mammography images. Further, the ultrasound images may be registered with the x-ray mammography images, as described in the '927 patent.

Figure 12:
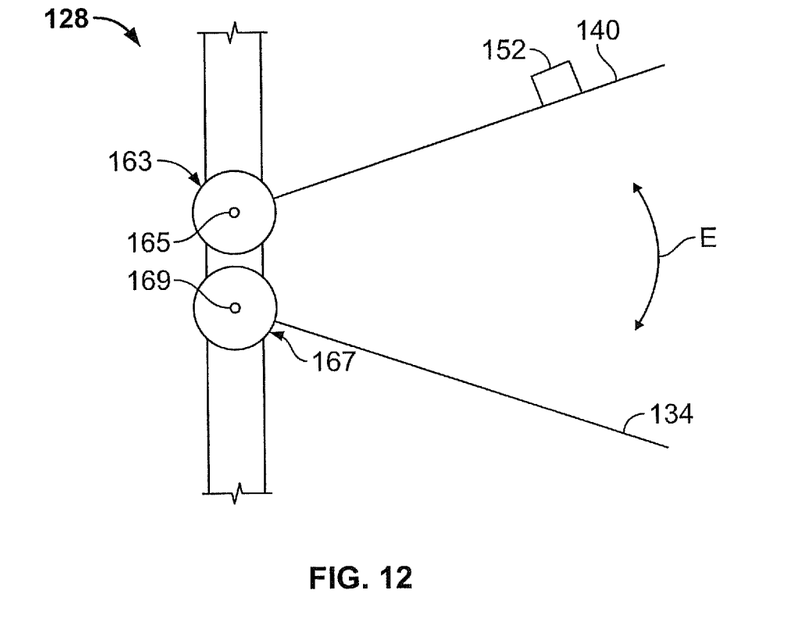
FIG. 12 illustrates a simplified representation of an ultrasound breast imaging assembly according to an alternative embodiment of the present invention.

FIG. 12 illustrates a simplified representation of an ultrasound breast imaging assembly 128 according to an alternative embodiment of the present invention. The ultrasound breast imaging assembly 128 may include an upper compression plate 140 operatively connected to an upper pivot assembly 163 having a axis 165, while the lower compression plate 134 is operatively connected to a lower pivot assembly 167 having a axis 169. The compression plates 134 and 140 may pivot about the pivoting axes 167 and 169, respectively, thereby moving with respect to one another in the direction of arc E. A probe 152 is positioned on the upper compression plate 140 and may move over the upper compression plate 140 similar to the probe 52 discussed above.

Figure 13:
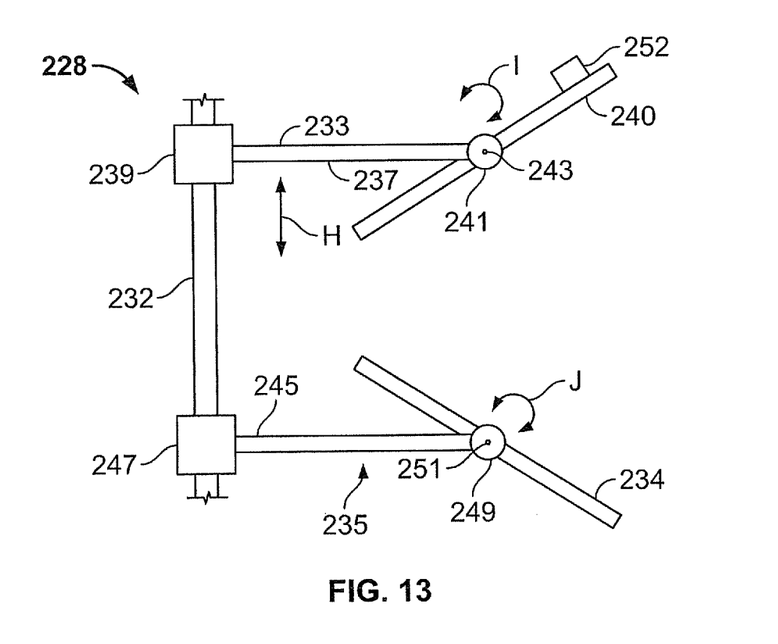
FIG. 13 illustrates a simplified representation of an ultrasound breast imaging assembly according to another alternative embodiment of the present invention.

FIG. 13 illustrates a simplified representation of an ultrasound breast imaging assembly 228 according to another alternative embodiment of the present invention. The ultrasound breast imaging assembly 228 includes an upper compressive member 233 and a lower compressive member 235, each secured to an upright member 232. Each compressive member 233 and 235 may move with respect to the upright member 232 in a direction denoted by H.

The upper compressive member 233 includes an extension member 237 connected to a translational assembly 239, which is translationally secured to the upright member 232. That is, the translational assembly 239 allows the upper compressive member 233 to move over the upright member 232 in the H direction. A pivotal compression plate 240 is pivotally secured to the extension member 237 through a pivot assembly 241 having an axis 243. The pivotal compression plate 240 may rotate about the axis 243 in the direction of I independent of the upper compressive member 233 moving in the direction of H. A probe 252 is positioned on the upper compression plate 240 and may move over the upper compression plate 240 similar to the probe 52, as discussed above.

The lower compressive member 235 includes an extension member 245 connected to a translational assembly 247, which is translationally secured to the upright member 232. That is, the translational assembly 247 allows the lower compressive member 235 to move over the upright member 232 in the H direction. A pivotal compression plate 234 is pivotally secured to the extension member 245 through a pivot assembly 249 having an axis 251. The pivotal compression plate 234 may rotate about the axis 251 in the direction of J independent of the lower compressive member 235 moving in the direction of H.

Figure 14:
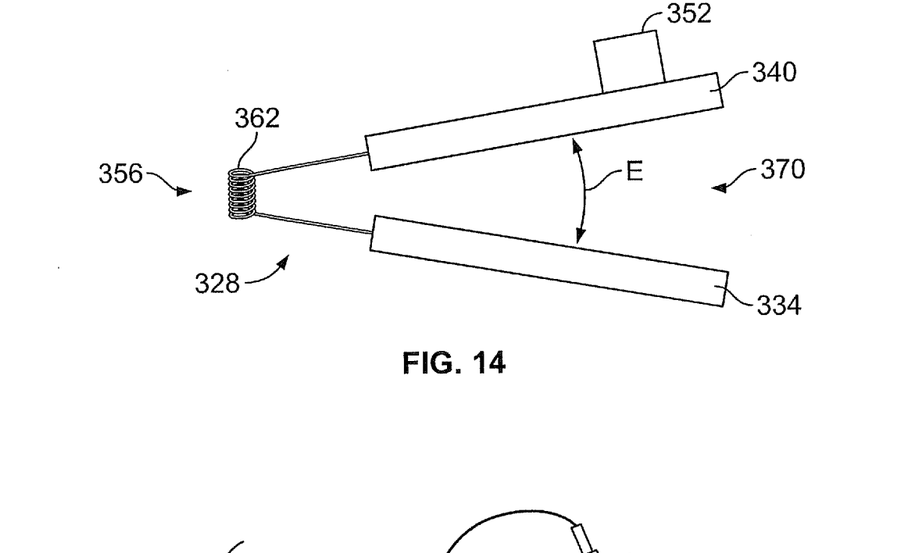
FIG. 14 illustrates a simplified representation of an ultrasound breast imaging assembly according to an additional alternative embodiment of the present invention.

FIG. 14 illustrates a simplified representation of an ultrasound breast imaging assembly 328 according to an additional alternative embodiment of the present invention. The ultrasound breast imaging assembly 328 includes an upper compression plate 340, having an ultrasound probe 352 positioned thereon, connected to a pivot assembly 356. Additionally, a lower compression plate 334 is connected to the pivot assembly 356. The pivot assembly 356 includes a spring member 362 that allows the compression plates 334 and 340 to be pivoted, or moved, with respect to one another. The spring member 362 has a force constant that maintains the compression plates 334 and 340 a defined distance from one another. For example, the force constant may cause the compression plates 334 and 340 to abut one another when a breast is not positioned within a breast compression area 370, which is defined between the compression plates 334 and 340.

In order to place a breast within the breast compression area 370, the compression plates 334 and 340 are separated, or moved apart, from one another. The breast is then positioned within the breast compression area 370. The force constant of the spring member 362 then causes the compression plates 334 and 340 to compress the breast. That is, the breast is sandwiched between the compression plates 334 and 340. Various spring members having various force constants may be used depending on a patient's preference and pain tolerance. Preferably, a spring member having a force constant that provides just enough force for sufficient compression for imaging (depending on the size and shape of the breast) may be used.

Thus, embodiments of the present invention provide a more patient-friendly ultrasound breast imaging assembly and system. Embodiments of the present invention also provide an ultrasound breast imaging system that automatically scans a patient's breast with more clarity and accuracy.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An ultrasound breast imaging assembly comprising:
   first and second compression plates that are angled with respect to one another;
   a breast compression area defined between said first and second compression plates;
   at least one pivot assembly allowing relative motion between said first and second compression plates, said at least one pivot assembly being operatively and directly connected to each of said first and second compression plates; and
   an ultrasound probe positioned on one of said first and second compression plates, said ultrasound probe being configured to translate over said one of said first and second compression plates.

2. The ultrasound breast imaging assembly of claim 1, wherein one of said first and second compression plates remains in a fixed orientation with respect to the other.

3. The ultrasound breast imaging assembly of claim 1, wherein the relative motion between said first and second compression plates occurs over an arcuate path.

4. The ultrasound breast imaging assembly of claim 1, wherein said at least one pivot assembly comprises a spring that connects said first compression plate to said second compression plate.

5. The ultrasound breast imaging assembly of claim 1, wherein said ultrasound breast imaging assembly comprises an upright member supported by a base, said first compression plate being operatively connected to a first pivot assembly, which is in turn connected to a first extension member, which is in turn translationally secured to said upright member.

6. The ultrasound breast imaging assembly of claim 5, wherein said second compression plate remains in a fixed orientation.

7. The ultrasound breast imaging assembly of claim 5, wherein said second compression plate is operatively connected to a second pivot assembly, which is in turn connected to a second extension member, which is in turn translationally secured to said upright member.

8. The ultrasound breast imaging assembly of claim 5, wherein said first extension member is perpendicular to said upright member, and wherein said first extension member translates along said upright member while said first and second compression plates remain angled with respect to one another, wherein the angle between the first and second compression plates changes when a breast is compressed therebetween.

9. The ultrasound breast imaging assembly of claim 1, wherein said first and second compression plates are configured to compress a breast in said breast compression area so that said probe may image the breast, and wherein said first and second compression plates remain angled with respect to one another, wherein the angle between the first and second compression plates changes upon the relative motion between the first and second compression plates.

10. The ultrasound breast imaging assembly of claim 1, wherein said first and second compression plates are radiolucent.

11. The ultrasound breast imaging assembly of claim 1, wherein said first and second compression plates are configured to adequately contact the breast for imaging even though the breast is not substantially flattened.

12. The ultrasound breast imaging assembly of claim 1, wherein said ultrasound breast imaging assembly is used in conjunction with an x-ray mammography system.

13. The ultrasound breast imaging assembly of claim 12, wherein said ultrasound breast imaging assembly is secured to a portion of said x-ray mammography system.

14. The ultrasound breast imaging assembly of claim 1, further comprising an upright member supported by a base, and a swivel member that connects said at least one pivot assembly and first and second compression plates to said upright member, wherein said swivel member is configured to rotate said first and second compression plates through a plurality of imaging orientations.

15. The ultrasound breast imaging assembly of claim 14, wherein said plurality of imaging orientations comprise a cranio-caudal (CC) orientation and a mediolateral oblique (MLO) orientation.

16. The ultrasound breast imaging assembly of claim 1, wherein said ultrasound breast imaging assembly is configured to allow a patient to be imaged in a standard mammography position.

17. The ultrasound breast imaging assembly of claim 1, wherein one of said first and second compression plates comprises a sonolucent compression film, and wherein said ultrasound probe is configured to translate over said sonolucent compression film.

18. The ultrasound breast imaging assembly of claim 1, wherein one of said first and second compression plates comprises a sound absorbing stabilization plate.

19. The ultrasound breast imaging assembly of claim 1, wherein the first and second compression plates remain angled with respect to one another during the relative motion between said first and second compression plates, and wherein the angle between said first and second compression plates changes during the relative motion between the first and second compression plates.

20. A breast imaging and display system comprising:
   a central processing unit (CPU);
   an imaging workstation in electrical communication with said CPU; and
   an ultrasound breast imaging assembly operatively connected to, and in electrical communication with, said CPU, said ultrasound breast imaging assembly comprising:
      an upper compression plate;
      a lower compression plate, wherein the planes of said upper and lower compression plates are angled with respect to one another;
      a breast compression area defined between said upper and lower compression plates;
      at least one pivot assembly allowing relative motion between said upper and lower compression plates while said planes of said upper and lower compression plates remain angled with respect to one another, said at least one pivot assembly being operatively and directly connected to each of said upper and lower compression plates, wherein the angle between said compression plates changes during the relative motion between said first and second compression plates; and
      an ultrasound probe positioned on one of said upper and lower compression plates, said ultrasound probe being configured to translate over said one of said upper and lower compression plates.

21. The system of claim 20, wherein said at least one pivot assembly comprises a spring that connects said upper compression plate to said lower compression plate.

22. An ultrasound breast imaging assembly comprising:
   first and second compression plates, said first and second compression plates being angled with respect to one another, one of said first and second compression plates comprising a sonolucent compression film, the other of said first and second compression plates comprising a sound absorbing stabilization plate;

a breast compression area defined between said first and second compression plates, wherein said first and second compression plates are configured to compress a breast in said breast compression area so that said probe may image the breast, and wherein said first and second compression plates remain angled with respect to one another during the compression;

at least one pivot assembly allowing relative motion over an arcuate path between said first and second compression plates, said at least one pivot assembly being operatively and directly connected to each of said first and second compression plates, and wherein the angle between the first and second compression plates changes upon the relative motion between the first and second compression plates; and an ultrasound probe positioned on one of said first and second compression plates, wherein said ultrasound probe is configured to translate over said one of said first and second compression plates.

23. The ultrasound breast imaging assembly of claim 22, wherein said at least one pivot assembly comprises a spring that connects said first compression plate to said second compression plate.

24. The ultrasound breast imaging assembly of claim 1, wherein said at least one pivot assembly comprises first and second pivot assemblies, wherein said first pivot assembly is operatively connected to said first compression plate, and said second pivot assembly is operatively connected to said second compression plate.

25. The ultrasound breast imaging assembly of claim 1, wherein said ultrasound breast imaging assembly comprises an upright member supported by a base, said first compression plate being operatively connected to a first pivot assembly, which is in turn positioned on a first portion of said upright member, said second compression plate being operatively connected to a second pivot assembly, which is in turn positioned on a second portion of said upright member.

26. The system of claim 20, wherein said at least one pivot assembly comprises upper and lower pivot assemblies, wherein said upper pivot assembly is operatively connected to said upper compression plate, and said lower pivot assembly is operatively connected to said lower compression plate.

27. The system of claim 20, wherein said ultrasound breast imaging assembly comprises an upright member supported by a base, said upper compression plate being operatively connected to an upper pivot assembly, which is in turn positioned on an upper portion of said upright member, said lower compression plate being operatively connected to a lower pivot assembly, which is in turn positioned on a lower portion of said upright member.

28. The system of claim 20, further comprising an upright member supported by a base, and a swivel member that connects said at least one pivot assembly and upper and lower compression plates to said upright member, wherein said swivel member is configured to rotate said upper and lower compression plates through a plurality of imaging orientations.

29. The ultrasound breast imaging assembly of claim 22, wherein said at least one pivot assembly comprises first and second pivot assemblies, wherein said first pivot assembly is operatively connected to said first compression plate, and said second pivot assembly is operatively connected to said second compression plate.

30. The ultrasound breast imaging assembly of claim 22, wherein said ultrasound breast imaging assembly comprises an upright member supported by a base, said first compression plate being operatively connected to a first pivot assembly, which is in turn positioned a first portion of said upright member, said second compression plate being operatively connected to a second pivot assembly, which is in turn positioned on a second portion of said upright member.

31. The ultrasound breast imaging assembly of claim 22, further comprising an upright member supported by a base, and a swivel member that connects said at least one pivot assembly and first and second compression plates to said upright member, wherein said swivel member is configured to rotate said first and second compression plates through a plurality of imaging orientations.

* * * * *